(12) United States Patent
Enggaard et al.

(10) Patent No.: US 9,114,211 B2
(45) Date of Patent: Aug. 25, 2015

(54) INJECTION DEVICE WITH VISUAL END-OF-CONTENT INDICATION

(75) Inventors: Christian Peter Enggaard, Vejby (DK); Tom Hede Markussen, Bagsvaerd (DK); Martin Von Bulow, Helsingoer (DK); Claus Schmidt Moeller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 1415 days.

(21) Appl. No.: 11/916,102

(22) PCT Filed: May 18, 2006

(86) PCT No.: PCT/EP2006/062407
§ 371 (c)(1),
(2), (4) Date: Jul. 9, 2008

(87) PCT Pub. No.: WO2006/128794
PCT Pub. Date: Dec. 7, 2006

(65) Prior Publication Data
US 2009/0137964 A1  May 28, 2009

Related U.S. Application Data

(60) Provisional application No. 60/686,552, filed on Jun. 2, 2005.

(30) Foreign Application Priority Data

May 31, 2005  (EP) ..................................... 05104671

(51) Int. Cl.
*A61M 5/178* (2006.01)
*A61M 5/315* (2006.01)
*A61M 5/20* (2006.01)

(52) U.S. Cl.
CPC ............ *A61M 5/178* (2013.01); *A61M 5/31553* (2013.01); *A61M 5/20* (2013.01); *A61M 5/31541* (2013.01); *A61M 5/31568* (2013.01); *A61M 5/31583* (2013.01)

(58) Field of Classification Search
CPC .............. A61M 5/24; A61M 5/31541; A61M 5/31585; A61M 2005/2488; A61M 5/31551; A61M 5/31525; A61M 5/21555; A61M 5/31581; A61M 5/178; A61M 5/31553; A61M 5/20; A61M 5/31568; A61M 5/31583
USPC .......... 604/134, 135, 207–211, 218, 225, 246
See application file for complete search history.

(56) References Cited

U.S. PATENT DOCUMENTS 5,480,387 A   1/1996  Gabriel et al.
5,584,815 A   12/1996 Pawelka et al.
(Continued)

FOREIGN PATENT DOCUMENTS

EP  0 327 910 B1  4/1992
EP  0 525 525 B1  5/1995
(Continued)

OTHER PUBLICATIONS

Search Examination Report issued in connection with counterpart European Application No. 05104671.2, mailed Sep. 6, 2005.
(Continued)

*Primary Examiner* — Theodore Stigell
*Assistant Examiner* — Lauren M Peng
(74) *Attorney, Agent, or Firm* — Wesley Nicolas

(57) ABSTRACT

An injection device (1) with an End-of-Content mechanism. The End-of-Content mechanism comprises a track (91) and a track follower each coupled directly or indirectly to the housing and the dose setting member (20). When setting a dose, the housing and the dose setting member is rotated relatively to each other thereby also rotating the track-follower in the track a distance corresponding to the size of the set dose. This relative rotation is summarized and stored in the position of the track follower in the track. The housing containing the mechanism is preferably equipped with a transparent (71) area through which a user can inspect the position of the track follower in the track and thereby get a visible warning when the drug reservoir in the injection device is about to be emptied.

8 Claims, 3 Drawing Sheets

(56) References Cited

U.S. PATENT DOCUMENTS

| | | | |
|---|---|---|---|
| 6,004,297 A | * | 12/1999 | Steenfeldt-Jensen et al. ............ 604/207 |
| 6,582,404 B1 | | 6/2003 | Klitgaard et al. |
| RE41,956 E | | 11/2010 | Klitgaard et al. |
| 2002/0120235 A1 | | 8/2002 | Enggaard |

FOREIGN PATENT DOCUMENTS

| | | |
|---|---|---|
| EP | 0 879 610 | 11/1998 |
| WO | WO 2004/007003 A1 | 1/2004 |
| WO | 2004/078240 A2 | 9/2004 |
| WO | WO 2004/078239 A1 | 9/2004 |
| WO | WO 2005/021072 A1 | 3/2005 |

OTHER PUBLICATIONS

International Search Report and Written Opinion issued in connection with counterpart International Application No. PCT/EP2006/062407, mailed Nov. 3, 2006.

International Preliminary Examination Report issued in connection with counterpart PCT Application No. PCT/EP2006/062407, mailed Dec. 21, 2007.

* cited by examiner

INJECTION DEVICE WITH VISUAL END-OF-CONTENT INDICATION

CROSS-REFERENCE TO RELATED APPLICATIONS

This application is a 35 U.S.C. §371 national stage application of International Patent Application PCT/EP2006/062407, filed May 18, 2006 (published as WO 2006/128794), which claimed priority of European Patent Application 05104671.2, filed May 31, 2005; this application further claims priority under 35 U.S.C. §119 of U.S. Provisional Application 60/686,552, filed Jun. 2, 2005.

THE TECHNICAL FIELD OF THE INVENTION

The invention relates to an apparatus such as an injection pen for delivering a drug to the human body and preferably such injection device equipped with an End-of-Content mechanism.

DESCRIPTION OF RELATED ART

In the disclosure of the present invention reference is mainly made to the treatment of diabetes by injection of insulin; however this is only an exemplary use of the present invention.

Injection pens are mainly made for users who have to inject themselves frequently, e.g. people suffering from diabetes. A number of demands are set to such injection pens. The setting of a dose must be easy and unambiguous and it must be easy to read the set dose. It must be possible with a minimum of trouble to cancel or change a wrongly set dose and when the dose is injected the dose setting must return to zero. When a prefilled injection pen is in question, i.e. an injection pen which is disposed of when the reservoir is empty, the injection pen must further be cheap and made of materials suitable for recycling.

Most dose setting devices work with a threaded piston rod co-operating with a nut where the nut and the piston rod may be rotated relative to each other. The dose setting may be obtained by screwing the nut away from a stop to which it is return during injection by pressing the piston rod forward until the nut member abuts the stop. By other dose setting devices one of the elements, the nut or the piston rod, is kept inrotatable and the other is allowed to rotate a set angle depending on the set dose, whereby the piston rod is screwed forward a distance through the nut member.

U.S. Pat. No. 5,480,387 disclose an injection device in which a piston rod moves a plunger forward inside a cartridge in order to expel the content of the cartridge. Once the piston rod is fully extracted and the plunger has reached the distal end of the cartridge, the cartridge is empty and no more drugs can be expelled. In order to visualize this to the user, the piston rod can be colour marked such that the colour appears in a window once the cartridge is empty. This however is only an indication showing that the cartridge is empty; it does not in itself prevent the user from attempting to set a dose. Neither does it prevent the user from setting a dose having a size larger than what is remaining in the cartridge which could lead to a potential dangerous situation especially if the user injects himself believing that the set dose is entirely expelled.

Should the user not notice that the cartridge has been emptied it is important when using such injection devices that the user can not set a dose that is lager than the content remaining in the reservoir.

A prior art delivery apparatus is disclosed in EP 327.910. This apparatus discloses a syringe by which a dose is set by screwing a nut member up along a threaded piston rod away from a stop in the housing. The set dose is injected by pressing the end of the nut member that forms an injection button axially back to abutment with the stop again. During this movement, the piston rod is carried along by the nut that does not move relative to this piston rod during injection. Since the thread of the piston rod has a length that corresponds to the length and content of the cartridge, the cartridge is just emptied when the nut is screwed to the end of the thread. Thereby the size of the dose to be set is limited to the remaining amount in the cartridge at all times.

A different injection device is disclosed in U.S. Pat. No. 6,582,404. In this solution a driver having a thread with a length corresponding to the amount of liquid in the reservoir to be emptied is surrounded by a dose setting member. The driver and the thread of the driver are coupled to the housing. A nut member is interfaced between the driver and the dose setting member. The nut member is engaged in the thread of the driver and is axially coupled to the dose setting member. In order to set a dose the dose setting element is rotated out of the housing of the injection device relatively to the driver. During this rotation the nut member coupled to the dose setting member is screwed up the thread coupled to the housing a distance corresponding to the set dose. When injecting the set dose, the dose setting member and the driver is rotated back into the housing such that the nut member maintain its relative position on the driver i.e. the nut member is kept inrotatable relatively to the thread of the driver. The position of the nut member in the thread will then at all times correspond to the accumulated set doses, and the nut member will engage the end of the track and lock the injection device when the accumulated set doses equals the initial content of the reservoir.

A similar solution is disclosed in WO 2004/078239. This injection pen comprises a threaded piston rod which is screwed forward in an internal threaded nut when rotated. A drive sleeve having a thread mating the thread of the piston rod rotates the piston rod when moved axially forward. The drive sleeve is coupled to a dose dial sleeve which is rotated relatively to the housing to dial up a dose. The dose dial sleeve is rotated out from the housing in order to set up a dose and it is rotated back to release the set dose. The drive sleeve is rotated together with the dose dial sleeve when a dose is set but prevented from rotation when the set dose is injected. This non-rotational movement of the drive sleeve forces the piston rod to rotate and to be screwed forward in the internal thread. The drive sleeve which is coupled to the dose dial sleeve is provided with a thread which corresponds to the amount of liquid in the cartridge. A nut engaging this thread is axially coupled to the housing such that the nut is screwed up the thread of the driver when a dose is set but maintained inrotatable in its relative position when the set dose is injected. The position of the nut will then at all times correspond to the accumulated set doses, and the nut will engage the end of the track and lock the injection device when the accumulated set doses equals the initial content of the cartridge.

All these so called End-of-Content mechanisms accomplish the aim of locking the dose setting mechanism of the injection device when the summarized set doses equals the initial amount of liquid in the reservoir. The user of such device is henceforth prevented in setting a dose that is larger than the amount of liquid remaining in the reservoir.

DESCRIPTION OF THE INVENTION

Having regard to the above-identified prior art devices, it is an object of the present invention to provide a drug delivery device having an End-of-Content mechanism which in addition to preventing the setting of a dose larger than the remaining amount in the reservoir also provides the user with a visual indication indicating that the end of content has been reached In an injection device comprising a housing and a dose setting member which is rotated relatively to the housing to set a dose, a track such as a helical thread can be coupled either to the housing or to the dose setting member and a track follower such as a nut member can be coupled to the other of the two parts.

When setting a dose the track and the track follower is rotated relatively to each other which will screw the track follower along the track a distance corresponding to the set dose.

The coupling need not be directly but could be through a series of different elements as long as the track follower is rotated relative to the track when a dose is set.

When injecting the dose, the track and the track follower is kept relatively inrotatable either by moving the track and the track follower simultaneously or by not moving them at all.

Since the track follower is kept in its relative position in the thread, the position of the track follower will at all time be an expression of the summarized set doses.

By having the length of the track correspond to the initial amount of liquid in the reservoir, the track follower will abut the end-wall of the track when the summarized set doses reaches the initial amount of liquid in the reservoir.

Since injection devices usually has a dose setting mechanism allowing the user both to dial up a dose and to dial down the dose prior to injecting the dose, the position of the track follower will be the position when the dose is injected whereby the position also expresses the injected dose.

By providing the housing with a transparent area in which the track follower is visible it will be possible for the user to inspect the position of the track follower in the track and thereby to visually see the summarized amount of set doses.

This area could e.g. be an opening in the housing or a transparent area through which the user can see the track follower or at least see a colour indication on the track follower.

The track follower could e.g. be provided with a colour or similar indication such that the user can get a visual indication through the area in the housing referred to. This colour indication can be made in different colours or with different intensity such that the visual impression delivered to the user changes according to the location of the track follower in the track and the position of the area in the housing.

In stead of colour indication other means of indication can be used e.g. numbers, letters or simply symbols.

In the End-of-Content mechanism disclosed in U.S. Pat. No. 6,582,404 and in WO 2004/078239 the dose setting member is rotated away from a fixed stop in the housing when a dose is set and returned back to the fixed stop when the dose is injected.

In U.S. Pat. No. 6,582,404 which is hereby incorporated by reference and which advantageously can be build into the injection device disclosed in FIGS. 15-17 in U.S. Pat. No. 6,004,297, the dose setting member is rotated back to its initial position when a dose is injected.

In WO 2004/078239 which is incorporated by reference, the dose setting member is also rotated back when a dose is injected, however the driver carrying the track and which is coupled to the dose setting member is moved axially back to its initial position.

When the track is coupled to the dose setting member e.g. via the driver as in WO 2004/078239 the area should be located in a position where the end of the track will stand when the dose setting member has been returned to its initial position.

The transparent area through which the user can inspect the track follower could stretch over a portion of the threads e.g. extend in a direction parallel to the piston rod, in which case the longitudinal displacement of the track follower is visible for a longer time prior to reaching the end of the track.

The transparent area could also be provided with a scale informing the user of the remaining content. The scale could be a traditional scale using numbers or it could be scale using other kind of symbols or different colours.

When the thread is coupled to the housing e.g. as in U.S. Pat. No. 6,582,404 where the driver via a piston rod guide is coupled to the housing, in can be necessary to provide an additional transparent area such as an opening in the dose setting member in order to make it possible for the user to visually inspect the track follower.

When there is no axial displacement of the dose setting member and the track is preferably provided on the inside of the housing, the area should be provided at the end of the track such that the track follower becomes visible when the summarized set doses starts to reach the initial amount of liquid in the reservoir.

DEFINITIONS

An "injection pen" is typically meant to be a mechanical i.e. user energized injection apparatus having an oblong or elongated shape somewhat like a pen for writing. Although such pens usually have a tubular cross-section, they could easily have a different cross-section such as triangular, rectangular or square.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1A:
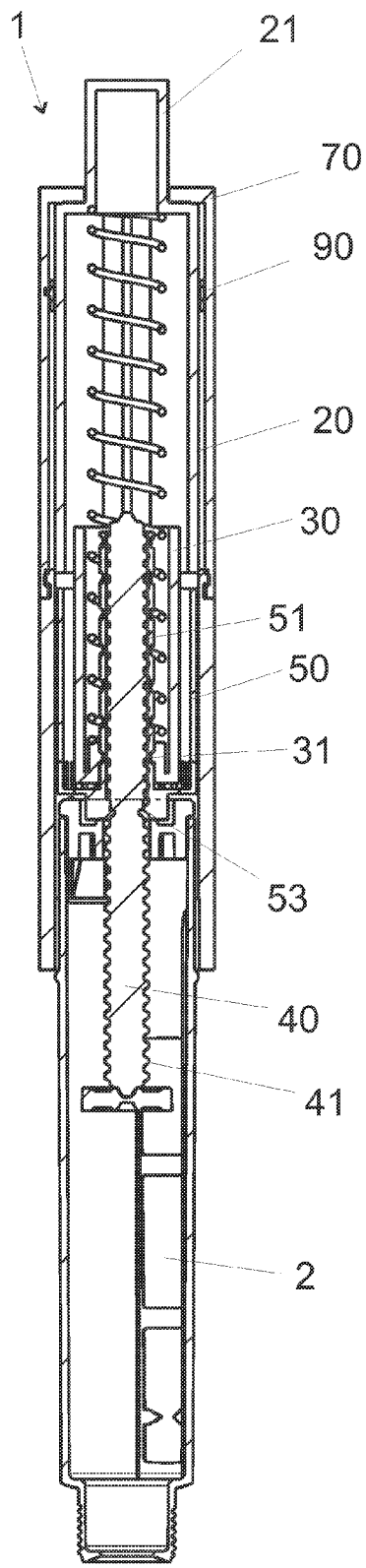
FIG. 1A+B shows a cross sectional view of part of the injection device.

FIG. 1 is a cross-sectional view of the dose setting and injection mechanism of an injection device 1 preferably an injection pen for subcutaneous injections. The injection device 1 comprises a dose setting member 20 being adapted to rotate about a centre axis of the injection device 1. It further comprises a dose indicator barrel 30, a threaded piston rod 40, a drive member 50 adapted to move the piston rod 40 along the centre axis, a helical spring 60 extending along and concentrically with the centre axis, and a housing 70.

The dose setting member 20 engages the dose indicator barrel 30 via a key 32 to keyway 22 connection. The key/keyway 32, 22 connection ensures that rotation of the dose setting member 20 about the centre axis causes rotation of the dose indicator barrel 30 about the centre axis, and vice versa. Furthermore, the key/keyway 32, 22 connection ensures that the dose setting member 20 and the dose indicator barrel 30 are slidable movable in relation to each other in a direction which is substantially parallel to the centre axis.

Similarly, the drive member 50 engages the outer threaded portion 41 of the piston rod 40 via a threaded portion 53 of the drive member 50.

The dose indicator barrel 30 is provided with a threaded portion 31 which engages a threaded portion 51 of the drive member 50.

Figure 1B:
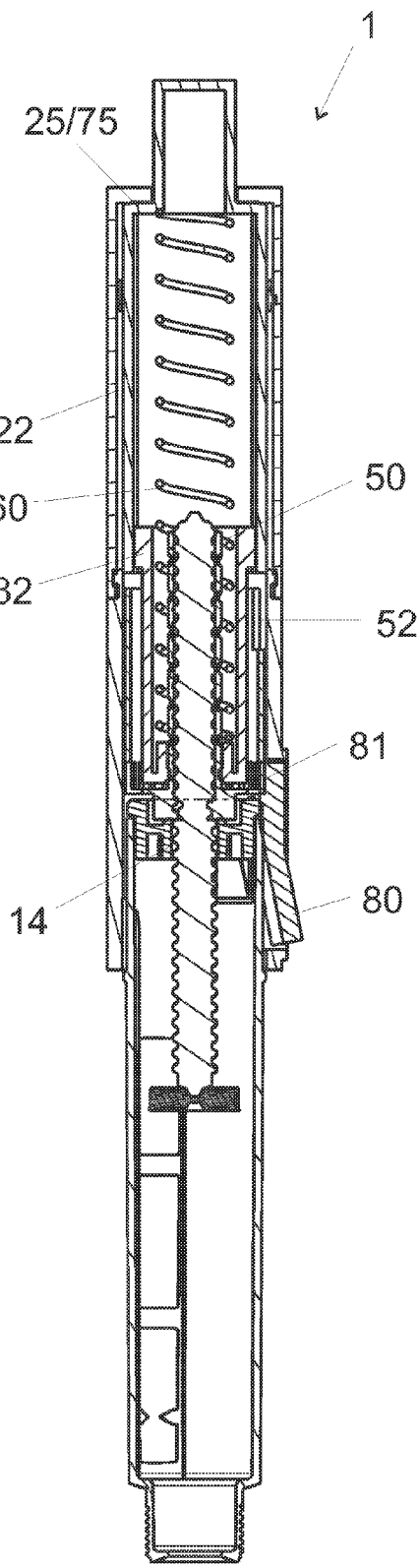

The injection device 1 is further provided with a locking member 80 which may be switched between a locking state and an unlocking state. When the locking member 80 is in its locking state (as shown in FIG. 1B) it prevents the drive member 50 from rotating about the centre axis e.g. by having a part 81 interacting with the drive member 50. On the other hand, when the locking member 80 is in its unlocking state, the drive member 50 is free to rotate about the centre axis. The dose setting member 20 is secured to the housing 70 via a toothing connection 25/75. The toothing connection 25/75 allows the dose setting member 20 and the housing 70 to be rotationally movable in relation to each. However, the helical spring 60 provides an axial force to the dose setting member 20 and presses the teeth 25 towards the teeth 75 internally in the housing 70 so that the dose setting member 20 remains in any set position.

The injection device 1 is preferably operated in the following manner. When a dose is to be set, the locking member 80 is switched to its locking state. In most cases, the locking state is the default position of the locking member 80. The user then causes the dose setting member 20 to rotate about the centre axis by turning a protruding part 21 of the dose setting member 20. Due to the key/keyway 22, 32 connection between the dose setting member 20 and the dose indicator barrel 30, the dose indicator barrel 30 is also caused to rotate about the centre axis. Since the threaded portion 31 of the dose indicator barrel 30 engages the threaded portion 51 of the drive member 50, this rotation forces the dose indicator barrel 30 in a direction parallel to the centre axis and towards the protruding part 21 of the dose setting member 20. Thus, the dose indicator barrel 30 performs a sliding movement along the key/keyway 22, 32 connection between the dose setting member 20 and the dose indicator barrel 30. This movement causes the helical spring 60 to be compressed, thereby storing energy in the spring 60. Thus, the dose is set without causing any changes to the outer appearance of the injection device 1, including no outward movement of the dose setting member 20.

The dose indicator barrel 30 is provided with a set of not shown numerals. As the dose indicator barrel 30 moves towards the protruding part 21 of the dose setting member 20, these numerals will be sequentially visible through a window 52 in the drive member 50, thereby indicating the dose which has been set. In order for the user of the injection device 1 to view the numerals on the dose indicator barrel 30, the housing 70 is equipped with a belt-like window aligned with the window 52 in the drive member 50.

When the desired dose has been set, an injection needle (not shown) positioned opposite the protruding part 21 of the dose setting member 20 is inserted into the skin of the user. Then the locking member 80 is switched to its unlocking state, thereby allowing rotation of the drive member 50 about the centre axis. Due to the energy stored in the compressed helical spring 60, the dose indicator barrel 30 is axially forced towards its initial position, i.e. away from the protruding part 21 of the dose setting member 20. Via the threaded portion 51 of the driver 50 and the threaded portion 31 of the dose indicator barrel 30, the drive member 50 is forced to rotate about the centre axis. When the drive member 50 and its thread 53 is rotated the piston rod 40, which is keyed, move forward inside the cartridge 2 due to a key connection 14 between the housing 70 and the piston rod 40. The axial movement of the piston rod away from the protruding part 21 causes the desired and set dose to be ejected from the injection device 1.

Alternatively, the drive member 50 may further comprise a key/keyway connection with the piston rod 40, and the key/keyway connection 14 between the housing 70 and the piston rod 40 may be replaced by a thread. In this case the piston rod 40 will rotate about the centre axis when the locking member 80 is switched to its unlocking state. The rotational movement causes the piston rod 40 to be screwed in a direction parallel to the centre axis and away from the protruding part 21 of the dose setting member 20. This movement will cause a dose to be ejected from the injection device 1.

When the dose has been ejected, the various parts of the injection device 1 are again in their initial position, except for the fact that the piston rod 40 has been moved in a direction away from the protruding part 21 of the dose setting member 20 due to the dose having been ejected and the angular position of the drive member 50 has changed relative to the housing 8. Thus, the injection device 1 is now ready for setting of a new dose.

Further, the end-of-content mechanism will be explained in relation to the FIGS. 2 to 4.

Figure 2:
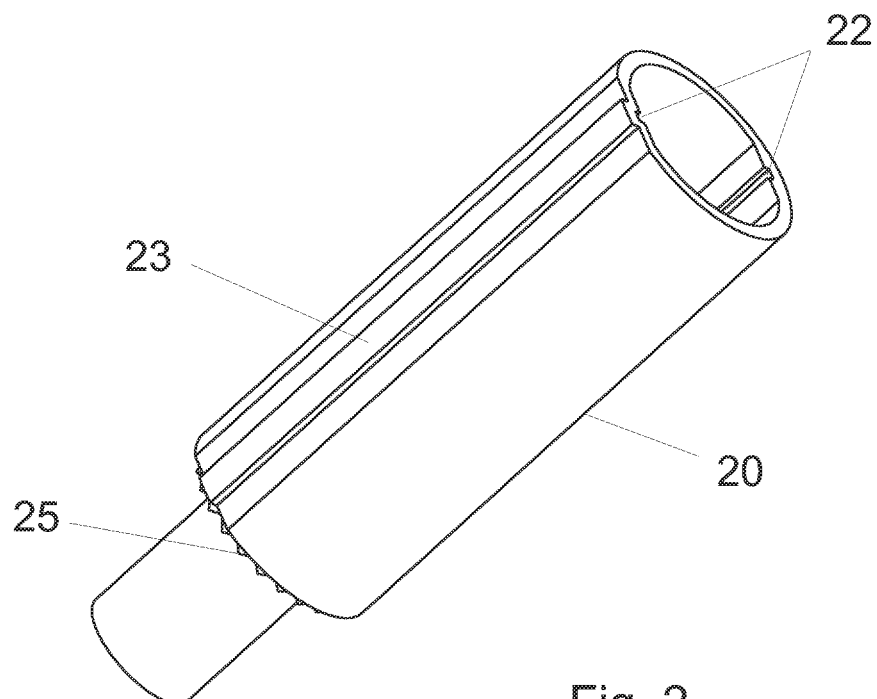
FIG. 2 shows a perspective view of the dose setting member.

FIG. 2 discloses the dose setting member 20 which has a longitudinal raised portion 23 which on the internal surface makes up a keyway 22. More than one such keyway 22 can be provided.

Figure 3:
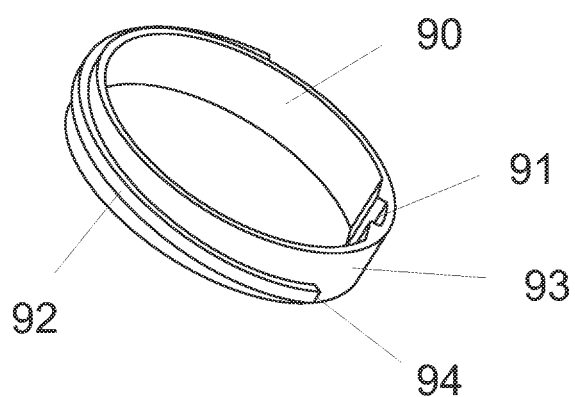
FIG. 3 shows a perspective view of the nut member.

FIG. 3 discloses a nut member 90 having an internal track 91 provided on the inside surface and a thread 92 provided on the outside surface. The thread 92 covers less than 360 degrees of the outside surface thereby leaving a part 93 of the outer surface without thread.

Figure 4:
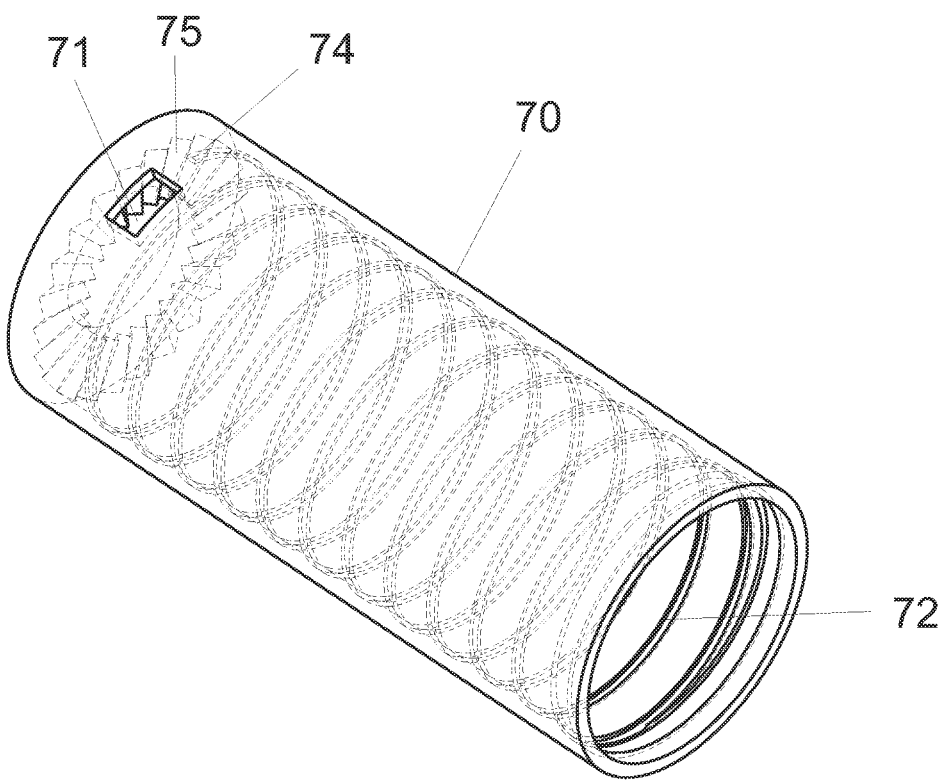
FIG. 4 shows a perspective view of part of the housing.

FIG. 4 discloses a part of the housing 70 having an opening 71 and an internal thread 72 provided on the inside surface.

The nut member 90 is as disclosed in FIG. 1 interfaced between the dose setting member 20 and the housing 70 with the internal track 91 engaging the raised portion 23 and the thread 92 engaging the internal thread 72 of the housing 70.

When a dose is being set by rotating the dose setting member 20, the nut member 90 is rotated up the internal thread 72 a distance corresponding to the set dose.

When the set dose is injected by releasing the spring 60, the nut member 90 remains in its position since the dose setting member 20 is not moved. The position of the nut member 90 in the internal thread 72 is therefore at any time an expression of the summarized set doses.

The internal thread 72 has a length which corresponds to the length the piston rod 40 has to travel in order to empty the reservoir 2, such that the stop 94 on the thread 92 engages the end-wall 74 in the internal thread 72 when the reservoir is empty thereby immobilising the dose setting and preventing the user from dialling up a dose larger than the remaining content of the reservoir.

In this end position the nut member 90 is visible through the transparent area 71 such that the user is informed that the reservoir is emptied.

Some preferred embodiments have been shown in the foregoing, but it should be stressed that the invention is not limited to these, but may be embodied in other ways within the subject matter defined in the following claims.

The invention claimed is:

1. An injection device for apportioning set doses of a liquid drug from a reservoir comprising:
 a housing supporting the reservoir,
 a dose setting member which is rotated relatively to the housing in order to set a dose,
 a piston rod or plunger (40) for moving forward in a cartridge to press medication out of the cartridge, wherein the piston rod does not rotate during the setting of a dose, which is accomplished by rotating the dose setting member,
 a track provided on an inside surface of the housing, which track has an end-wall defining a length that corresponds to the initial amount of liquid in the reservoir, and
 a track follower coupled to both the housing and the dose setting member, which track follower engages the track, whereby the track and the track follower are rotated relatively to each other when a dose is set and kept relatively irrotatable when the set dose is injected such that the track follower is moved along in the track when setting a dose having a position in the track representing the summarized set doses,
 and whereby the track follower engages the end-wall of the track when the summarized set doses equals the initial amount of liquid in the reservoir thereby preventing a user from setting a dose larger than the remaining content of the reservoir,
 wherein the housing is provided with a transparent area in which the track follower is visible.

2. The injection device according to claim 1, wherein the visibility of the track follower changes according to the remaining content in the reservoir.

3. The injection device according to claim 1, wherein the dose setting member is rotated away from a fixed stop in the housing when a dose is set and returned back to the fixed stop when the set dose is injected.

4. The injection device according to claim 1, wherein the area is located in the close proximity of the end-wall of the track.

5. The injection device according to claim 1, wherein the area stretches over a portion of the track.

6. The injection device according to claim 1, wherein an additional area in the dose setting member is provided.

7. The injection device according to claim 1, wherein the dose setting member is rotated relatively to the housing without any axial displacement when a dose is set.

8. The injection device according to claim 7, wherein the track is provided on the inside surface of the housing.

* * * * *